(12) United States Patent
Garabet

(10) Patent No.: US 7,689,285 B2
(45) Date of Patent: Mar. 30, 2010

(54) MULTI-LAYER COMBINATION OF AN ELECTRIC STIMULATION ELECTRODE AND A WOUND DRESSING

(75) Inventor: Luca Garabet, Hamburg (DE)

(73) Assignee: GerroMed Pflege und Medizintechnik GmbH & Co. KG, Hamburg (DE)

( * ) Notice: Subject to any disclaimer, the term of this patent is extended or adjusted under 35 U.S.C. 154(b) by 1014 days.

(21) Appl. No.: 10/544,439

(22) PCT Filed: Feb. 5, 2004

(86) PCT No.: PCT/EP2004/001059
§ 371 (c)(1),
(2), (4) Date: Aug. 3, 2005

(87) PCT Pub. No.: WO2004/069088
PCT Pub. Date: Aug. 19, 2004

(65) Prior Publication Data
US 2006/0189912 A1    Aug. 24, 2006

(30) Foreign Application Priority Data
Feb. 7, 2003    (DE) ............... 203 01 973 U

(51) Int. Cl.
*A61F 15/00* (2006.01)
(52) U.S. Cl. .............. 607/50; 607/1; 607/2; 607/3; 607/152; 602/41; 602/42; 602/43; 602/48
(58) Field of Classification Search ............... 607/1–3, 607/50, 152–153; 602/41–43, 48
See application file for complete search history.

(56) References Cited

U.S. PATENT DOCUMENTS

| | | | | |
|---|---|---|---|---|
| 3,964,477 | A * | 6/1976 | Ellis et al. | ............ 604/20 |
| 5,269,810 | A * | 12/1993 | Hull et al. | ............ 607/129 |
| 6,235,047 | B1 * | 5/2001 | Augustine et al. | ............ 607/96 |
| 6,263,226 | B1 | 7/2001 | Axelgaard et al. | |
| 2002/0151951 | A1 | 10/2002 | Axelgaard et al. | |

FOREIGN PATENT DOCUMENTS

| | | |
|---|---|---|
| DE | 195 37 579 A1 | 10/1997 |
| DE | 201 03 311 U1 | 6/2001 |
| DE | 20 301 873 U1 | 7/2004 |
| EP | 03 67 320 A1 | 5/1990 |
| EP | 0504 715 A.1 | 9/1992 |
| WO | PCT/EPO2/01731 | 9/2002 |
| WO | WO 02 068045 | 9/2002 |

* cited by examiner

*Primary Examiner*—Carl H Layno
*Assistant Examiner*—Deborah Malamud
(74) *Attorney, Agent, or Firm*—Kelly Lowry & Kelley, LLP

(57) ABSTRACT

In order to make available a wound dressing (100) with at least one energy transfer agent (11, 12) and a wound dressing (13), namely a combination of wound dressing and electrode for the stimulation treatment, with which an uniform electro-stimulation of the wound can be achieved so that the wound healing process is considerably improved, it is proposed that the energy transfer agent has at least two layers and that the energy transfer agent (11, 12) has at least two adjacent layers (11, 12), a first layer (11)—energy supply—and a second energy—distribution of energy—(12), whereby the first layer (11) has a lower electric resistance and the second layer (12) a higher electric resistance.

21 Claims, 2 Drawing Sheets

MULTI-LAYER COMBINATION OF AN ELECTRIC STIMULATION ELECTRODE AND A WOUND DRESSING

TECHNICAL FIELD

This invention starts from a wound dressing according to the preamble of claim 1.

PRIOR ART

From the prior art electrostimulation apparatuses are known which are used for the treatment of wounds, in particular of bad healing chronic wounds.

In the EP 0 504 715 A1, a wound treatment device is described which consists of an electrically non conductive layer which has an opening and of an electrically conductive non metallic material. Moreover, the wound treatment device has a substantially non adhering wound contact layer.

From the DE 201 03 311 US we know a wound coating which consists of a combination of an energy transfer agent and at least one wound coating means. Here an electrode is used as energy transfer agent. However, the disadvantage of this device is that a homogeneous current distribution cannot be achieved by the electrode used. The electrodes used in the prior art, in particular close to the points of contact to which the current of the respective electrode is supplied, show current peaks so that an uniform eletrostimulation of the wound surface is consequently not possible. This results to the fact that in particular large surface injury wounds cannot be treated uniformly by such a wound coating.

DESCRIPTION OF THE INVENTION, AIM, SOLUTION, ADVANTAGES

The aim of this invention is to make available a combination of wound dressing and electrode for the stimulation treatment which an uniform electrostimulation of the wound can be achieved so that the wound healing process is considerably improved.

A wound dressing with the characteristics of claim 1 is proposed to achieve this aim.

According to the invention, a novel wound dressing with an energy transfer agent, consisting of an energy supplying layer and an energy distribution layer, a wound coating and a protection and fixation layer is created which is used for the stimulation treatment, in particular with electrostimulation apparatuses.

To this purpose, it is foreseen according to the invention that the energy transfer agent has at least two adjacent layers, a first energy supplying layer and a second energy transferring layer. This being, it is of essential importance that the first layer has a lower electric resistance and the second layer a higher electric resistance. Due to such a configuration, it has shown that a homogeneous current distribution can be reached over the whole surface of the energy transfer agent. This being, the first layer which has a lower electric resistance provides the homogeneity. Then, the current flows into the second layer adjacent to the first layer which has a higher resistance.

Contrary to the known wound electrodes, it is thus possible with the subject of the invention to achieve a nearly uniform energy loaded stimulation treatment of the wound so that the wound healing process is considerably improved.

Preferable further developments of the wound dressing are described in the claims.

In a preferred embodiment, the first layer has a protection and fixation layer on the side opposite to the second layer. A wound coating which rests directly on the wound to be treated is appropriately placed on the side of the second layer which is opposite to the first layer. One of the advantages of the wound dressing according to the invention is that the wound coating which serves for the protection and the care of the wound surface, must not, contrary to the known wound devices, be expressly removed for a stimulation treatment, which would not be beneficial to the healing process of the wound. For each change of the wound dressing is always connected—despite of a thorough cleaning of the wound—with a risk of infection. But the would dressing according to the invention remains on the wound to be treated, even if no stimulation treatment is carried out. Besides the saving of dressing material, a considerable reduction of the treatment time through the nursing staff is achieved due to the wound dressing according to the invention.

Preferably the first layer is a silver layer so that a low electric resistance is obtained in the first layer. The incoming current is homogenously distributed in the silver layer over the whole surface of the energy transfer agent because of its good electrically conductive properties and then arrives over the second layer into the wound coating. Thus, the silver layer constitutes an effective means of the wound dressing according to the invention in order to obtain an uniform stimulation treatment of the wound to be dressed. Furthermore, due to the use of the silver layer there results the possibility to place a current feed at any point of the energy transfer agent since an optimal current distribution is guaranteed even for a lateral arrangement or for example at a corner of the energy transfer agent. Current peaks are nearly avoided by this wound dressing according to the invention. An additional advantage of the silver layer is that it has an antimicrobial effect which is particularly positive in the healing process of wound surfaces.

According to the invention, it is foreseen that the wound coating is hydrophilic and electrically conductive, whereby the wound coating can be a gel, in particular a hydrogel. It is also conceivable to use hydrocolloids, alginates or polyurethane foams as wound coating. Contrary to the known inactive wound coatings, in particular gauze compresses, pads or absorbent nonwovens, the afore mentioned wound coatings, in particular hydrogels are to be preferred for the treatment of damaged skin and wounds. The advantage of their use is, among others, that they have a good biological tolerance, in particular when they are applied during a longer period of time. Because of the hydrophilic property, the wound coating can absorb liquid such as wound exudat (protein containing liquid which comes out from the vessels by inflammations) in bigger quantities by an increase in volume without losing its coherence. Furthermore, due to the homogeneous electric conductivity of the wound coating, the electrostimulation can easily pass through and arrives uniformly to the wound area to be treated. It is particularly advantageous that due to the electrostimulation of the wound coating or of the wound heat is fed as well so that, according to medical findings, a better and quicker healing process is obtained.

In particular due to the exclusion of atmospheric oxygen from the wound, the healing process can be further accelerated because the wound is forced to bring oxygen into the wound area over the blood. This takes place by an increased formation of new vessels so that the wound healing is improved. This being, hydrogel as well as hydrocolloids, alginates or polyurethane foams are appropriate means to create such nearly oxygen-free conditions in the wound.

In a further preferred embodiment of the wound dressing, the wound coating can have wound healing promoting substances. This being, the substances are preferably growth factors. While the wound coating rests on the wound area to be treated and absorbs wound exudate, it simultaneously sets wound healing promoting substances free for the wound so that the healing process of the wound is accelerated. In particular for bad healing chronic wounds, a wound coating with wound healing promoting substances is advantageous.

An electrode for the electrostimulation can be used as energy transfer agent for the wound dressing according to the invention. It is also conceivable to configure the energy transfer agent as a foil. Appropriately the energy transfer agent has an electrical connecting means which can be connected with the energy producer which supplies the wound dressing during the stimulation treatment with current or with electric pulses. Preferably the connecting means is placed on the first layer which goes for example through an opening provided in the protection/fixation layer above and which can be connected with the energy producer. Preferably metal or an electrically conductive synthetic material, in particular rubber, is conceivable for the energy transfer agent.

Furthermore, the wound dressing has on the side opposite to the energy transfer agent an additional layer which is preferably a peelable foil. Such a layer protects the wound coating from impurities. The foil can be easily removed from the wound dressing before applying onto the wound area. This being it is advantageous if the foil preferably made of polyethylene, polypropylene or polyurethane is impermeable to water and active substances. After the foil has been removed from the wound dressing, the wound dressing according to the invention is applied onto the wound. The wound coating appropriately has adhesive properties on its surface opposite to the wound so that a reliable application on the wound surface is guaranteed.

It is particularly advantageous that the wound dressing is flexible and elastic so that it can be adapted to the contour of the human body, in particular to special parts of the body.

SHORT DESCRIPTION OF THE DRAWINGS

The invention will be explained in detail below with reference to the attached drawings.

PREFERRED EMBODIMENT OF THE INVENTION

Figure 1:
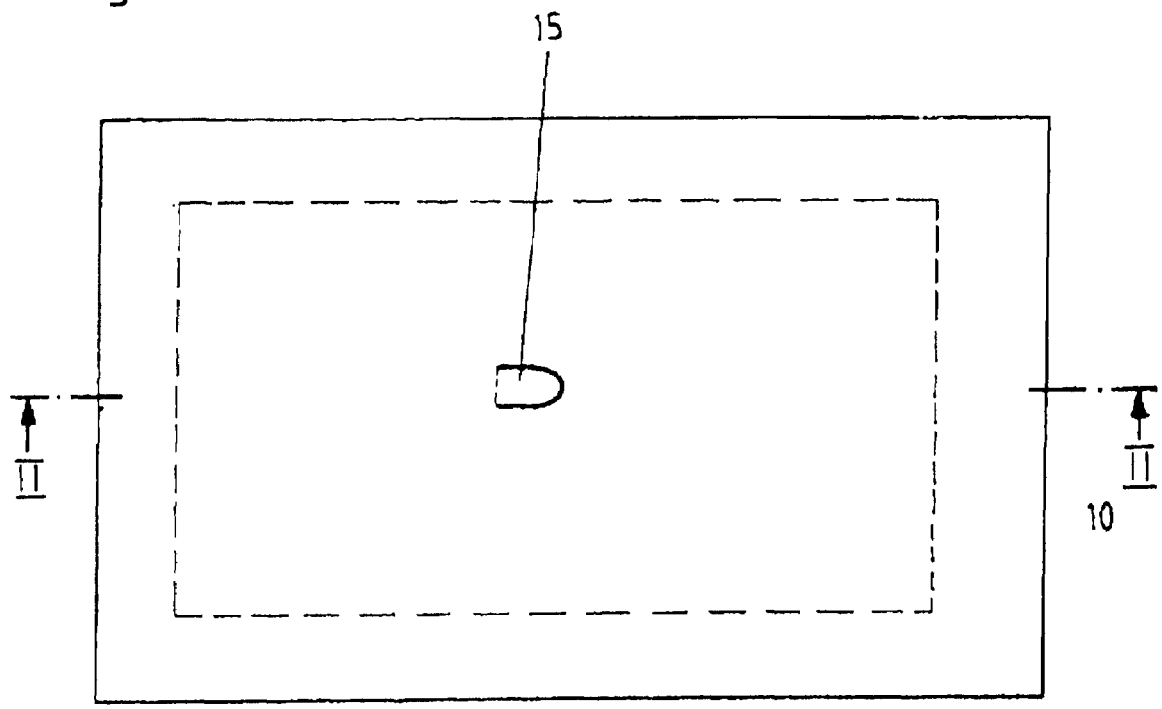
FIG. 1 shows a top view of an embodiment of a wound dressing according to the invention.
Figure 2:
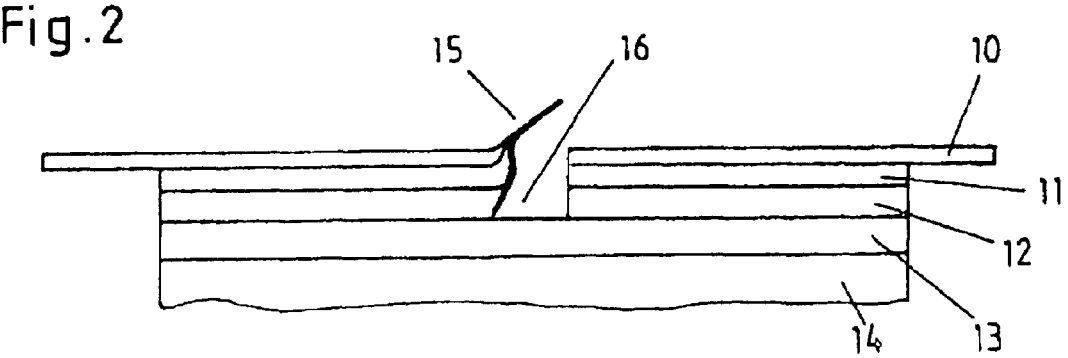
FIG. 2 shows a pure schematic section according of line II-II of the wound dressing according to the invention according to FIG. 1.

FIGS. 1 and 2 show a preferred embodiment of a wound dressing according to the invention 100. The wound dressing 100 has an energy transfer agent 11, 12 in form of a two-layer electrode which is configured with a first—energy supplying—layer 11 and a second—energy distributing—layer 12. These layers 11, 12 rest on each other with their upper faces. In order to guarantee an uniform current distribution on the surface of the energy transfer agent 11, 12, the first layer 11 is a silver layer. The aim of this is that this layer is of low impedance or that it has a lower electric resistance. On the side opposite to the second layer 12, a protection/fixation layer 10 which covers the energy transfer agent 11, 12, is placed on the first layer 11 so that the energy transfer agent is fixed on the surrounding skin. This being, the non electrically conductive protection/fixation layer 10 consists of plastic foil type material. It is also possible to make the protection/fixation layer 10 for example of plaster foil type or foam foil type material.

An opening 16 which is illustrated in particular in FIG. 2 is placed for the represented embodiment on the protection/fixation layer 10 in order to be able to realize an electrical connection with the electrode 11, 12 covered by the protection/fixation layer 10. An electrical contact 15 which consists of the first and second layer 11/12 passes through the opening 16. Like in the represented embodiment, the opening 16 can be configured for example as a shackle which can be bent up. The end of the electrical contact 15 can be connected with an energy producer which however is not shown in the figures.

A wound coating 13 which is a gel 13 in the represented embodiment is placed below the second layer 12—on the side opposite to the first layer 11. This gel is hydrophilic and electrically conductive and can contain wound healing promoting substances. The gel 13 is in direct contact with the wound/skin 14. However, before the wound dressing 100 is applied on the wound 14, a foil (which is not represented) is removed which is placed on the surface of the gel 13 and thus protects the gel 13 from impurities. However, it is important that a slight stripping of the foil is possible without removing areas from the wound coating 13 at the same time. The foil is configured impermeable to water and active substances so that the wound dressing 100, in particular the gel 13, does not lose liquid or the wound healing promoting substances during storage.

After the foil has been removed, the wound dressing 100 is applied onto the wound to be treated 14. The gel has adhesive properties on its surface so that it remains sticked efficiently on the skin/wound 14—even over longer periods of time.

During the stimulation treatment, the wound dressing 100 is loaded with current, in particular with pulses. This being, the current flows from the energy producer over the electrical contact 15 into the first layer—energy supply—11 of the electrode 11, 12. Because of the low resistance of the first layer 11, the current is uniformly distributed and flows then into the second layer—energy distribution—12 with the higher resistance. From there the electronic stimulation is further transmitted by the subjacent gel 13 which has a homogeneous electrical conductivity—to the wound 14 so that an uniform stimulation over the wound surface 14 can be achieved with the represented embodiment.

During the stimulation treatment, the gel 13 can release wound healing promoting active substances to the wound 14 so that the healing process can be accelerated. Simultaneously the gel 13 is able, because of its composition, to absorb wound exudate in higher quantities. This being, the absorbency of liquid (such as water oder wound exudate) is guaranteed by absorbers. Polymers are for example appropriate as absorbers. Moreover, the gel 13 has a stable structure, in particular during the stimulation treatment of the wound 14 and during the resting on the wound 14.

Figure 3:
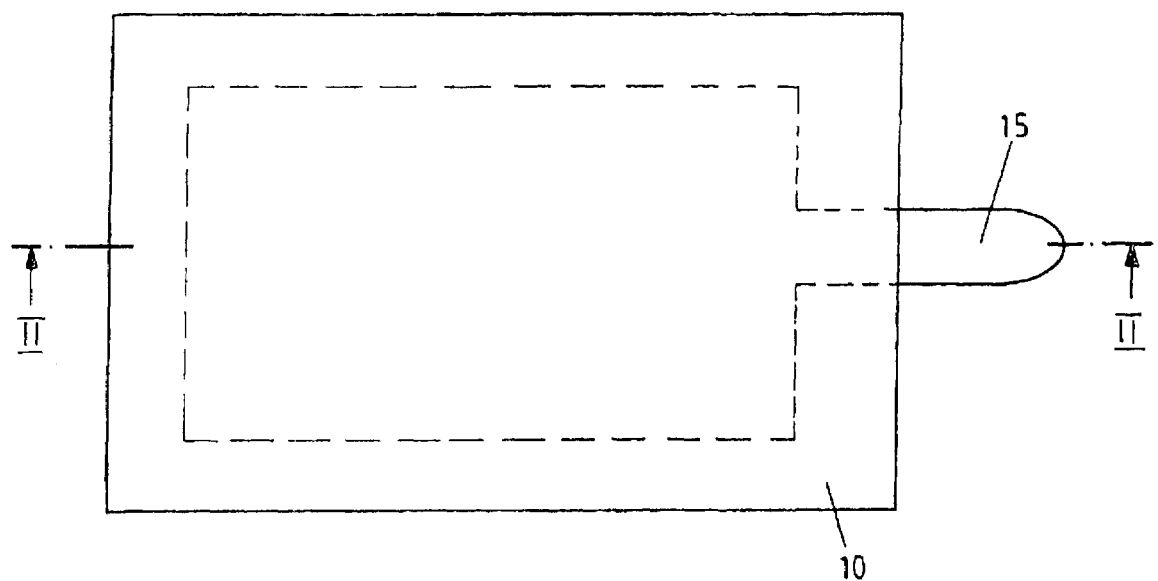
FIG. 3 shows a top view of a second embodiment of a wound dressing according to the invention.
Figure 4:
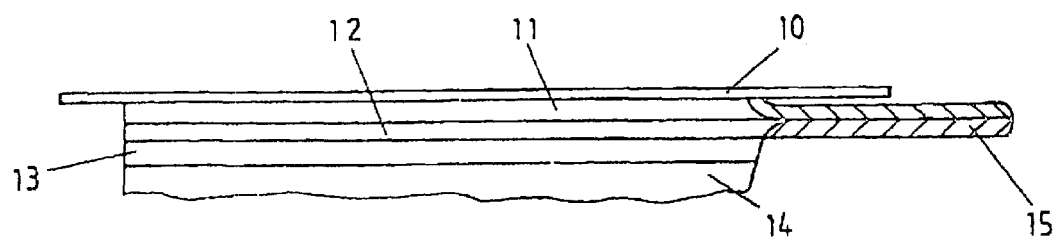
FIG. 4 shows a pure schematic section according to line III-IV of the wound dressing according to the invention according to FIG. 3.

FIGS. 3 and 4 show a further preferred embodiment of the wound dressing 100. The same parts have the same reference numerals as the corresponding parts in FIGS. 1 and 2 and the same description is valid for them. The difference consists in the lateral arrangement of the electrical contact 13 which serves as connecting means and which is here connected with the layers 11, 12 by being laterally led through.

LIST OF REFERENCE NUMERALS

100 Wound dressing
10 Protection/fixation layer
11 First layer of the energy transfer agent—energy supply
12 Second layer of the energy transfer agent—energy distribution
13 Wound coating/gel
14 Skin, wound
15 Connecting means, electrical contact
16 Opening

The invention claimed is:

1. A wound dressing, comprising:
an electrical energy transfer medium comprising an electrode for electrostimulation of a wound, said electrode having multiple adjacent layers, including a first layer having a first electric resistance and adapted to provide an energy supply with a generally homogenous current distribution across a total area of the energy transfer medium and a second layer for distribution of energy, wherein the second layer has a higher second electric resistance than the first layer;
a protection/fixing layer disposed on a side of the first layer generally opposite to the second layer; and
a wound pad on a side of the second layer generally opposite the first layer and adapted for direct contact with the wound, wherein the wound pad is electrically conductive, heat conducting or heat generating when energy is applied thereto.

2. A wound dressing according to claim 1, wherein the first layer comprises a silver.

3. A wound dressing according to claim 1, wherein the wound pad is hydrophilic.

4. A wound dressing according to claim 1, wherein the wound pad is electrically conductive.

5. A wound dressing according to claim 1, wherein the wound pad has adhesive properties.

6. A wound dressing according to claim 1, wherein the wound pad is a hydrogel, hydrocolloid, alginate or a polyurethane foam.

7. A wound dressing according to claim 1, wherein the wound pad includes a wound healing promoting substance.

8. A wound dressing according to claim 7, characterized in that the wound healing promoting substance is a growth factor.

9. A wound dressing according to claim 7, wherein the wound substance comprises an antibiotic, antiseptic, vitamin, or an analgesic.

10. A wound dressing according to any of claims 1, 2-4 or 7-9, characterized in that the first and second layers comprise a metal foil or an electrically conductive plastic, rubber, silicone or synthetic material.

11. A wound dressing according to any of claims 1, 2-4 or 7-9, characterized in that the energy transfer medium includes an electrical connecting means which can be connected with an energy producer.

12. A wound dressing according to any of claims 1, 2-4 or 7-9, characterized in that the connecting means is placed on the first layer.

13. A wound dressing according to any of claims 1, 2-4 or 7-9, characterized in that the connecting means is placed on the first and second layer.

14. A wound dressing according to claim 1, characterized in that the protection/fixation layer is configured with an opening.

15. A wound dressing according to claim 1, characterized in that the protection/fixation layer is made of self-adhesive water vapour permeable material.

16. A wound dressing according to claim 1, characterized in that the wound pad has an additional layer on the side opposite to the second layer.

17. A wound dressing according to claim 16, characterized in that the additional layer is a peelable foil.

18. A wound dressing according to claim 17, characterized in that the foil is made of polyethylene, polypropylene or polyurethane.

19. A wound dressing according to either of claims 17 or 18, characterized in that the foil is impermeable to water and active substances.

20. A wound dressing according to claim 1, characterized in that the wound pad has self-adhesive properties.

21. A wound dressing according to any of claims 1, 2-4 or 7-9, characterized in that the wound dressing is flexible and elastic.

* * * * *